US00PP21107P3

(12) United States Plant Patent
Klemm et al.

(10) Patent No.: US PP21,107 P3
(45) Date of Patent: Jun. 29, 2010

(54) POINSETTIA PLANT NAMED 'NPCW08153'

(50) Latin Name: *Euphorbia pulcherrima (Willd.)*
Varietal Denomination: NPCW08153

(75) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 78 days.

(21) Appl. No.: 12/288,736

(22) Filed: Oct. 23, 2008

(65) Prior Publication Data

US 2010/0107289 P1 Apr. 29, 2010

(51) Int. Cl.
*A01H 5/00* (2006.01)

(52) U.S. Cl. ..... Plt./307

(58) Field of Classification Search ..... Plt./307
See application file for complete search history.

(56) References Cited

U.S. PATENT DOCUMENTS

PP16,870 P2 * 7/2006 Klemm ..... Plt./307
PP19,094 P2 * 8/2008 Dummen ..... Plt./307

OTHER PUBLICATIONS

Canadian PBR application available at http://www.inspection.gc.ca/english/plaveg/pbrpov/cropreport/poi/app00007030e.shtml accessed Mar. 4, 2010.*

* cited by examiner

*Primary Examiner*—Wendy C. Haas
(74) *Attorney, Agent, or Firm*—Jondle & Associates, P.C.

(57) ABSTRACT

A new poinsettia plant particularly distinguished by a medium early flowering season, medium vigor, with medium to large bracts, thick and upright v-shaped stems and a brilliant bract color is disclosed.

1 Drawing Sheet

Poinsettia Plant Named 'NPCW08153'

Genus and species

*Euphorbia pulcherrima* (Willd.)

Variety denomination

'NPCW08153'

BACKGROUND OF THE NEW PLANT

The present invention comprises a new and distinct cultivar of poinsettia plant, botanically known as *Euphorbia pulcherrima* (Willd.) and hereinafter referred to by the cultivar name 'NPCW08153'. The new cultivar is the result of a natural pollination between the female parent poinsettia plant 'NPCW04097' (U.S. Plant Pat. No. 16,870) and an unnamed male poinsettia plant conducted in December 2004 in Kenya.

The new cultivar has been asexually reproduced over six generations by vegetative cuttings in Stuttgart, Germany starting in April 2007. The cultivar has proved to be stable and uniform. The present invention has been found to retain its distinctive characteristics through successive asexual propagations.

Plant Breeder's Rights for this cultivar were applied for in Canada on Dec. 10, 2007. 'NPCW08153' has not been made publicly available more than one year prior to filing of this application.

SUMMARY OF THE INVENTION

The following are the most outstanding and distinguishing characteristics of this new cultivar when grown under normal horticultural practices in Stuttgart, Germany.

1. A medium early flowering season;
2. Medium vigor;
3. Medium to large bracts;
4. Thick and upright stems (V-shaped); and
5. Brilliant bract color.

DESCRIPTION OF PHOTOGRAPH

This new poinsettia plant is illustrated by the accompanying photograph which shows overall plant habit including blooms, buds, and foliage of the plant; the colors shown are as true as can be reasonably obtained by conventional photographic procedures. The photograph is of a whole plant about three-months-old and in full flower, grown in a greenhouse in Stuttgart, Germany, in December of 2007.

DESCRIPTION OF THE NEW CULTIVAR

The following detailed description sets forth the distinctive characteristics of 'NPCW08153'. The data which define these characteristics were collected from asexual reproductions carried out in Stuttgart, Germany. The plant history was taken on four month-old plants from August to December 2007 with a minimum pinch date of 33 weeks. The plants were grown in a greenhouse covered with glass. Color readings were taken under natural light in the greenhouse. Color references are primarily to the RHS Colour Chart of The Royal Horticultural Society of London (RHS) (2001).

DETAILED BOTANICAL DESCRIPTION OF THE NEW PLANT

Classification:
*Family.*—Euphorbiaceae.
*Botanical.*—*Euphorbia pulcherrima.*
*Common.*—*Poinsettia.*

Parentage:
*Female parent.*—'NPCW04097' (U.S. Plant Pat. No. 16,870).
*Male parent.*—Unnamed male *poinsettia* plant.
Growth:
*Time to produce a rooted cutting.*—About 12 days.
*Blooming habit.*—Intermittent.
*Flowering response time.*—Approximately 7.5 weeks.
*Keeping quality.*—About 25 days.
Plant:
*Form.*—Triangular.
*Growth habit.*—Upright.
*Height.*—22.0 cm to 28.0 cm.
*Width.*—26.0 cm to 30.0 cm.
*Number of branches.*—4 to 6.
*Average number of inflorescences per plant.*—5.
Stems:
*Color.*—Lower part: RHS 143A and RHS 183A. Upper part: RHS 143A and RHS 183A.
*Length.*—About 22.0 cm.
*Internode length.*—2.0 cm to 5.0 cm.
*Diameter.*—0.5 cm to 1.0 cm.
Leaves:
*Quantity.*—8 to 12 per lateral branch.
*Arrangement.*—Alternate.
*Shape.*—Ovate.
*Base.*—Obtuse.
*Apex.*—Acute.
*Lobes.*—Present, lobation is slight.
*Margin.*—Serrate.
*Texture.*—Upper surface: Smooth Lower surface: Smooth
*Vein color.*—Upper surface: RHS 139A. Lower surface: RHS 181A and RHS 139D.
*Variegation.*—Absent.
*Size.*—Length: 4.0 cm to 10.0 cm. Width: 3.0 to 8.0 cm.
*Color.*—Mature foliage: Upper surface: RHS 139A. Lower surface: RHS 137B. Immature foliage: Upper surface: RHS 144B. Lower surface: RHS 143C.
*Leaf petiole.*—Length: 2.0 cm to 4.0 cm. Diameter: 0.2 cm to 0.3 cm. Color: Upper surface: RHS 45C. Lower surface: RHS 143A at the petiole base narrowing and turning RHS 45C towards the tip. Texture: Smooth.
*Aspect.*—Horizontally directed, leaf blades slanting somewhat downward.
Inflorescence:
*Inflorescence type.*—Intermittent.
*Lastingness.*—About 4 weeks.
*Diameter.*—15.0 cm to 20.0 cm.
*Height of inflorescence.*—2.0 to 5.0 cm.
Bracts:
*Number of bracts per inflorescence.*—6 to 8.
*Shape.*—Ovate.
*Base.*—Obtuse.
*Apex.*—Acute.
*Lobes.*—Present, lobation is slight.
*Size.*—Length: 6.0 cm to 10.0 cm. Width: 4.0 cm to 7.0 cm.
*Texture.*—Smooth.
*Vein color.*—Upper surface: RHS 53A. Lower surface: RHS 53B.
*Bract color.*—Upper surface: RHS 46B. Lower surface: RHS 46B.
*Bract petiole.*—Length: 1.0 cm to 3.0 cm. Diameter: 0.2 cm. Color: Upper surface: RHS 53B. Lower surface: RHS 143C at the petiole base narrowing and turning RHS 53B towards the tip.
Cyme:
*Diameter.*—1.0 cm to 2.0 cm.
*Cyathia number.*—4 to 6 per inflorescence.
*Cyathium.*—Shape: Ovate. Diameter: 0.3 cm to 0.5 cm. Length: 0.4 cm to 0.7 cm. Color: RHS 143C.
*Peduncle.*—Color: RHS 143C. Length: 0.1 cm to 0.2 cm.
*Nectar cups.*—Number: 1 per cyathia. Diameter: 0.1 cm. Size: 0.2 cm long. Color: RHS 15B.
Reproductive organs:
*Stamens.*—Quantity: 5 to 10 per cyathia. Shape: Ovate. Pollen: Quantity: Low. Color: Between RHS 9A and 12A.
*Gynoecium.*—Present.
Fruit and seed set: No fruit or seed have been observed
Disease and insect/pest resistance: Good

COMPARISON WITH PARENTAL AND COMMERCIAL CULTIVARS

'NPCW08153' differs from the female parental poinsettia plant 'NPCW04097' (U.S. Plant Pat. No. 16,870) by having a medium to bright-red bract color while 'NPCW04097' has a very dark-red bract color. 'NPCW08153' has a flowering response time of 7.5 weeks while 'NPCW04097' has a flowering response time of more than 8 weeks. Additionally, 'NPCW08153' has medium sized bracts while 'NPCW04097' has small bracts.

'NPCW08153' differs from the commercial cultivar 'Premium' (unpatented) by having more vigor, smaller bracts and less cyathias than 'Premium'.

I claim:

1. A new and distinct cultivar of poinsettia plant as shown and described herein.

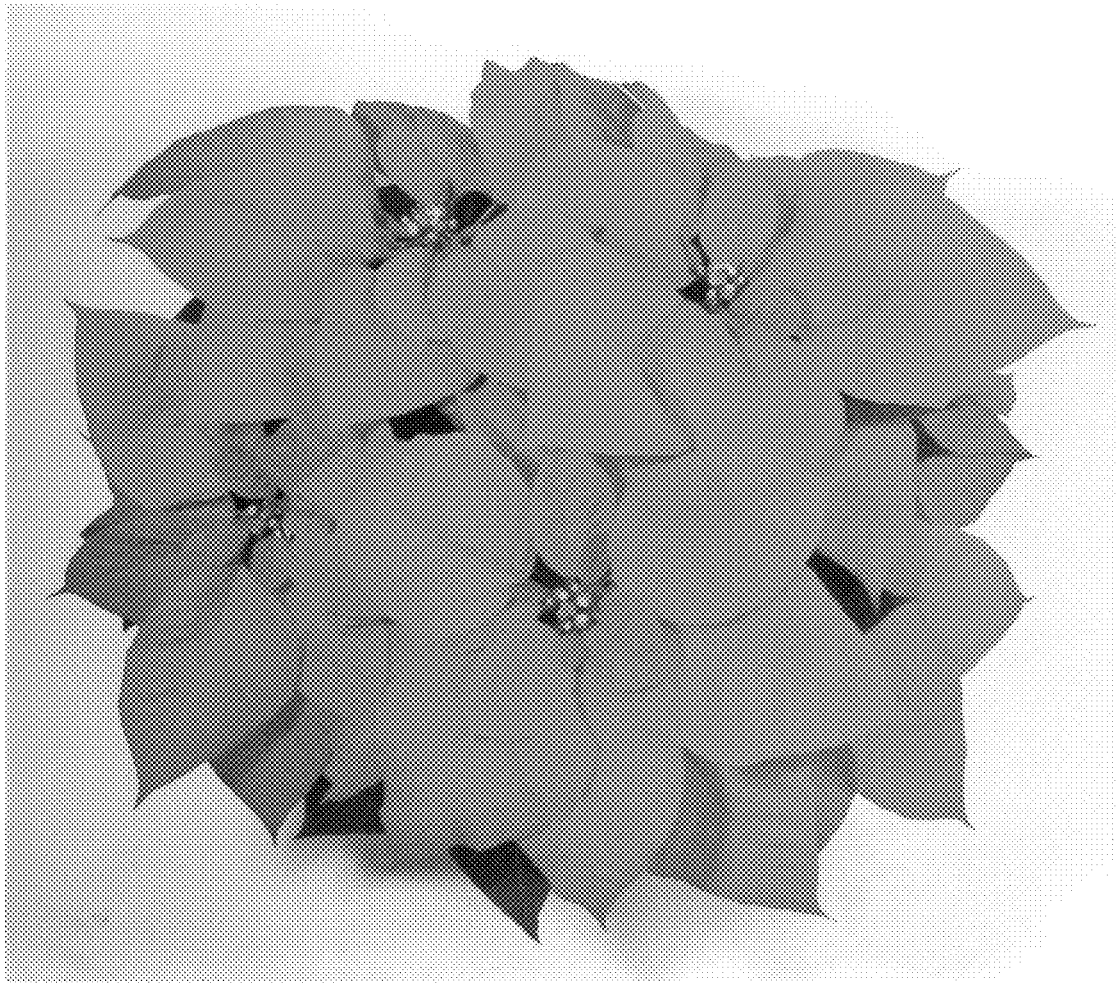

* * * * *